(12) United States Patent
Bauer et al.

(10) Patent No.: US 10,207,032 B2
(45) Date of Patent: Feb. 19, 2019

(54) SMALL-VOLUME COLLECTION FOR A BREASTPUMP SYSTEM

(71) Applicant: Medela Holding AG, Baar (CH)

(72) Inventors: Ryan Bauer, Fox River Grove, IL (US); Jahi Gist, McHenry, IL (US); Brian H. Silver, Cary, IL (US); David Cho, McHenry, IL (US); Ron Sallade, McHenry, IL (US); Kathryn Holshouser, Woodstock, IL (US)

(73) Assignee: Medela Holding AG (CH)

( * ) Notice: Subject to any disclaimer, the term of this patent is extended or adjusted under 35 U.S.C. 154(b) by 0 days.

(21) Appl. No.: 14/211,363

(22) Filed: Mar. 14, 2014

(65) Prior Publication Data

US 2014/0276629 A1 Sep. 18, 2014

Related U.S. Application Data

(60) Provisional application No. 61/786,176, filed on Mar. 14, 2013.

(51) Int. Cl.
*A61M 1/06* (2006.01)
*A61M 1/00* (2006.01)

(52) U.S. Cl.
CPC ............ *A61M 1/0033* (2014.02); *A61M 1/06* (2013.01); *A61M 1/007* (2014.02); *A61M 2205/3331* (2013.01); *A61M 2205/3379* (2013.01)

(58) Field of Classification Search
CPC ...... A61M 1/06; A61M 1/0031; A61M 1/062; A61M 1/064; A61M 1/066; A61M 1/068; A61M 1/03; A61M 1/0033; A61M 1/0077; A61M 2205/3331; A61M 2205/3379; A61M 1/007; A61M 39/105; A61J 9/00; A61J 9/06; A61J 9/08; A23C 9/206

USPC ..... 604/73, 74, 513, 75, 67, 514; 206/459.1, 206/427; 215/11.1, 11.5
See application file for complete search history.

(56) References Cited

U.S. PATENT DOCUMENTS

| | | | |
|---|---|---|---|
| 4,323,067 A * | 4/1982 | Adams | A61M 1/06 604/346 |
| 4,573,969 A * | 3/1986 | Schlensog | A61M 1/06 604/231 |
| 4,583,970 A | 4/1986 | Kirchner | |
| 4,772,262 A * | 9/1988 | Grant | A61M 1/064 604/74 |

(Continued)

FOREIGN PATENT DOCUMENTS

| | | |
|---|---|---|
| EP | 2412392 A1 | 2/2012 |
| WO | 2012014135 A1 | 2/2012 |

OTHER PUBLICATIONS

International Search Report for International Application PCT/US14/27803 dated Nov. 14, 2014.

(Continued)

*Primary Examiner* — Imani N Hayman
*Assistant Examiner* — Tiffany Legette
(74) *Attorney, Agent, or Firm* — McDonnell Boehnen Hulbert & Berghoff LLP (57) ABSTRACT

Exemplary systems for small volume collection for a breastpump system are provided. The systems allow breast milk to flow directly from the breastshield to the collection container without leaving the control volume. A valve is present outside of the milk flow path that does not contact breast milk prior to the milk reaching a collection vessel.

7 Claims, 7 Drawing Sheets

(56) References Cited

U.S. PATENT DOCUMENTS

| | | | |
|---|---|---|---|
| 4,929,229 A | 5/1990 | Larsson | |
| 5,071,403 A * | 12/1991 | Larsson | A61M 1/06 604/320 |
| 5,431,680 A * | 7/1995 | Jones | A61J 7/0053 604/210 |
| 5,941,847 A * | 8/1999 | Huber | A61M 1/066 604/74 |
| 6,042,560 A | 3/2000 | Niederberger | |
| 6,361,524 B1 * | 3/2002 | Odell | A61M 5/3129 604/181 |
| 2004/0127845 A1 | 7/2004 | Renz et al. | |
| 2004/0133151 A1 | 7/2004 | Watanabe | |
| 2005/0154348 A1 * | 7/2005 | Lantz | A61M 1/066 604/74 |
| 2009/0099511 A1 | 4/2009 | Sutrina et al. | |
| 2010/0121266 A1 | 5/2010 | Bryan | |
| 2010/0268189 A1 * | 10/2010 | Byrnes | A61M 37/00 604/506 |
| 2012/0265169 A1 * | 10/2012 | Sherman | A61M 1/06 604/514 |
| 2012/0279941 A1 * | 11/2012 | Sprehe | A61J 9/001 215/365 |
| 2012/0289936 A1 * | 11/2012 | Ingram | A61J 15/00 604/514 |
| 2012/0315353 A1 * | 12/2012 | Becsi | A61J 9/00 426/2 |

OTHER PUBLICATIONS

U.S. Appl. No. 61/475,578, filed Apr. 14, 2011.
U.S. Appl. No. 61/780,804, filed Mar. 13, 2013.

* cited by examiner

SMALL-VOLUME COLLECTION FOR A BREASTPUMP SYSTEM

CROSS-REFERENCE TO RELATED APPLICATIONS

This application claims priority to U.S. Provisional Patent Application Ser. No. 61/786,176 filed on Mar. 14, 2013, which is hereby incorporated by reference in its entirety.

BACKGROUND

Unless otherwise indicated herein, the materials described in this section are not prior art to the claims in this application and are not admitted to be prior art by inclusion in this section.

When directly breastfeeding an infant is not feasible or desirable, a breastpump system can be used to express breast milk into a collection container. The collected breast milk may be used right away or may be stored for later use.

Breastpump systems typically include a breastshield to interface with the breast, a connector piece attached to a pump via tubing, and an outlet valve provided in the milk flow path to separate the pump's volume to which vacuum is applied (also known as the control volume or working volume) from the atmosphere as well as from the collection container downstream of the outlet valve. Separating the collection container from the control volume via the outlet valve generally serves to prevent undesirable vacuum level changes.

In the early days or weeks after delivery of an infant, the maternal milk supply is limited and includes colostrum. Colostrum production for some mothers may be as low as mere drops of the fluid per breast per pumping session, for example. For some mothers, for example, colostrum production may be less than 5 mL. Colostrum ingestion in the very earliest stages of post-partum life is considered to be highly valuable to the newborn infant. Colostrum is known to contain different content from mature breast milk. Colostrum contains antibodies that are major components of the immune system, anti-inflammatory agents, and growth factors that stimulate the development of the gut.

Colostrum also has unique physical properties as compared to mature breast milk, including higher viscosity and surface adhesion. Such properties often cause colostrum to become trapped by the various breastpump components, such as the connector and the valve or sticking directly to a surface, for example, reducing the amount of colostrum collected in the collection container. Because of the low volumes and the high nutritional and immunological value associated with colostrum production, reduced colostrum yield through the breastpump system due to trappings within the milk flow path may be more of an issue than a loss of mature milk for a more mature baby.

Additionally, during expression of mature milk, lower-fat foremilk is first expressed, followed by higher-fat hindmilk. If one wanted to observe the transition from foremilk to hindmilk, taking portions of expressed milk at discrete time points during the pumping process may be required. This type of portioning would be inconvenient given current systems. Such portions may be desired for analysis or for storage and later administration, such as administering higher-fat milk to babies that require high calorie feedings for example.

SUMMARY

The present disclosure is directed to a breastpump system for small volume collection that provides a simplified breast milk flow path, allowing breast milk to flow directly from the breastshield to a collection container without leaving the pump's control volume. In the present breastpump system described herein, a relief valve is present, outside of a simplified milk flow path, which does not contact breast milk prior to the milk reaching a collection vessel.

In one aspect, a system for milk collection is provided. The system comprises a breastshield and connector assembly, having a first opening at a first end configured to receive at least part of a woman's breast, a second end comprising a second opening configured to receive a connection to a vacuum source, and a third opening distal to the first end. A first container for collection of milk having a port is attachable to the third opening and is in fluid communication with the third opening when attached. A breastmilk bottle may also be present as a second collection container and may be attached to the breastshield and connector assembly through a fourth opening.

In another aspect, a method is provided. The method comprises receiving expressed breast milk via a breastshield and connector assembly, providing a first flow path through an interior of the breastshield and connector assembly and via a hole into a first collection container, and providing a second flow path through the interior of the breastshield and connector assembly, a valve, and into a second collection container. At least a portion of the second flow path follows the first flow path. The second flow path extends across at least a portion of the hole.

In another aspect, a method is provided. The method comprises receiving expressed breast milk via a breastshield of a breastshield and connector assembly, providing a first flow path through an interior of the breastshield into a hole of the breastshield and connector assembly, and collecting the expressed breast milk into a syringe-style container coupled to the hole.

In yet another aspect, a breastpump kit is provided. The breastpump kit comprises a breastshield for receiving expressed breast milk therethrough, a connector attached to the breastshield and configured for fluid communication with a source of vacuum, a valve in fluid communication with the connector and an atmosphere outside of the breastpump kit, and a container. The expressed breast milk moves along a flow path from the breastshield through the connector and into the container, and does not flow through the valve.

These as well as other aspects, advantages, and alternatives, will become apparent to those of ordinary skill in the art by reading the following detailed description, with reference where appropriate to the accompanying drawings.

DETAILED DESCRIPTION

Example breastpump systems are described herein. It should be understood that the words "example" is used herein to mean "serving as an example, instance, or illustration." Any embodiment or feature described herein as being an "example" is not necessarily to be construed as preferred or advantageous over other embodiments or features. In the following detailed description, reference is made to the accompanying figures, which form a part thereof. In the figures, similar symbols typically identify similar components, unless context dictates otherwise. Other embodiments may be utilized, and other changes may be made, without departing from the spirit or scope of the subject matter presented herein.

The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Overview

The present disclosure provides a simplified flow path through a breastpump system. Such a simplified flow path may facilitate collection of small volumes of liquid (small volume collection), for example. A collection vessel or container may be present inside the pump's working volume (also known as the control volume) and may be tailored for a typical colostrum or otherwise smaller liquid collection. Although the system may be optimized for small volume collection, it may be used for any volume of liquid collection where simplification of the flow path is desired. Maximizing yield of small volumes of expressed milk while preserving breastpump functionality may be desired in collecting colostrum, taking discrete milk samples or portions, or other applications.

Figure 1:
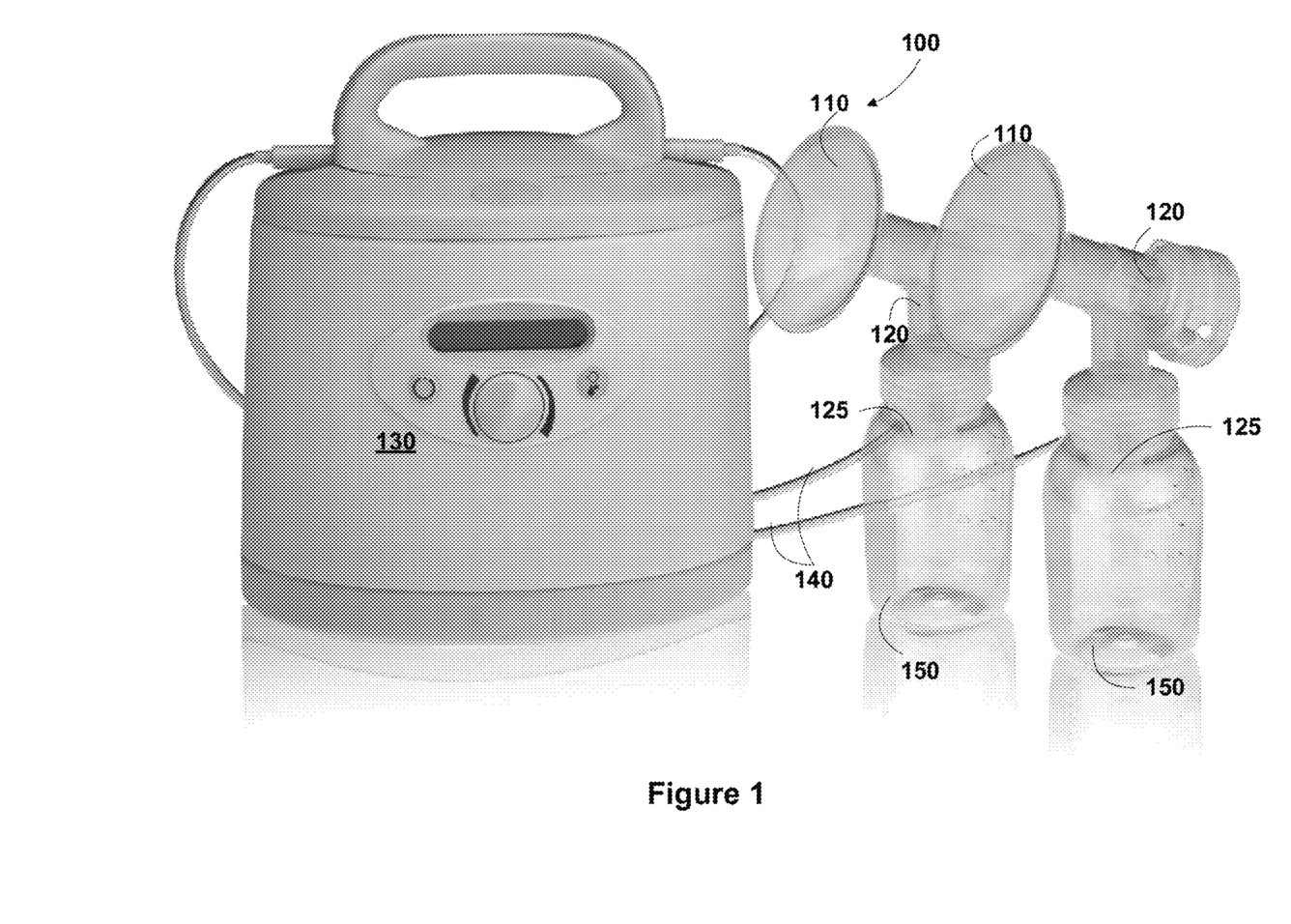
FIG. 1 is a perspective view of an example breastpump system, in accordance with an example embodiment.

FIG. 1 is a perspective view of an example breastpump system 100, in accordance with an example embodiment. The breastpump system 100 comprises breastshields 110 assembled to connectors 120, valves 125, and tubing 140 attached to both the connectors 120 and a pump 130. The breastpump system 100 is an electrically-driven breastpump that further includes an electric motor that plugs into standard house current and/or operates off of battery power. Collection containers 150 are attached to the connectors 120.

The basic construction and operation of breastpump systems or assemblies are well known in the art, such as the breastpumps described in U.S. Pat. Nos. 6,547,756, 7,727,182, and 6,387,072, which are hereby incorporated by reference in their entirety.

I. Example Small Volume Collection Containers and Systems

Figure 2A:
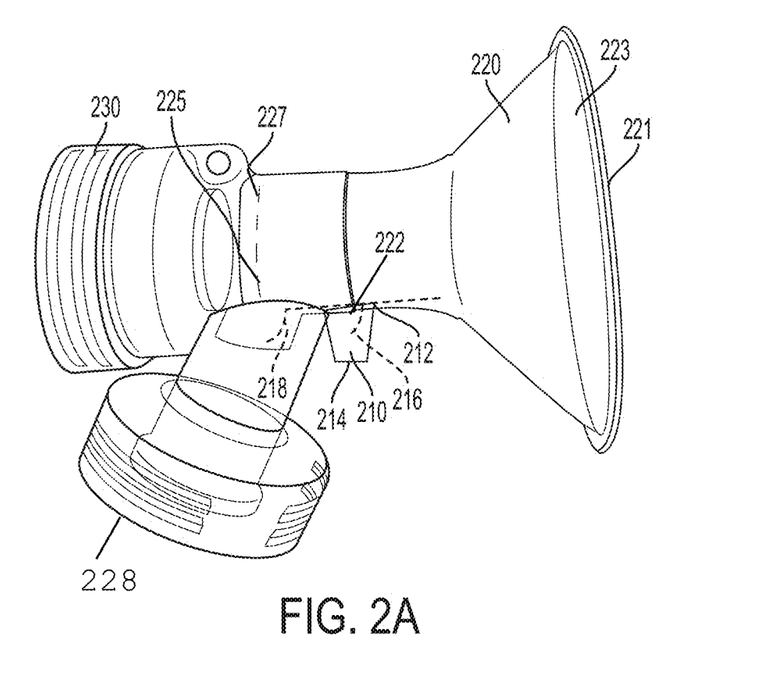
FIG. 2A is a side view of a small volume collection container with a breastshield and connector assembly, in accordance with an example embodiment.

FIG. 2A is a side view of a first collection container 210 with a breastshield and connector assembly, comprising a breastshield 220 and a connector 230, in accordance with an example embodiment. The first collection container 210 may be a small volume collection container.

The connector 230 is also shown attached to the breastshield 220 at the distal end of the breastshield 220. The connector 230 may be attached to a pump (such as a pump for generating a vacuum) via tubing, as depicted in FIG. 1. The pump and tubing may be the same as or similar to the pump 130 and tubing 140 of FIG. 1. In an alternative embodiment, the pump may comprise a manually driven breastpump.

The breastshield 220 comprises a first opening 221 at a first end 223 and a second opening 225 at a second end 227. A third opening 222 may be present in the breastshield as shown in FIG. 2A. In another embodiment, the third opening 222 may be present in the connector 230 or at a junction between the connector and breastshield. The first opening 221 is configured to receive at least part of a woman's breast. The second opening 225 is configured to mate the connector 230 and may be positioned so as to be substantially in-line with at least a portion of the first opening 221. In the embodiment shown in FIG. 2A, the third opening 222 extends through a side of the breastshield 220, however, as previously discussed, the third opening 222 may extend through a side of the connector 230 or through a junction between the connector 230 and the breastshield 220. The third opening 222 is shown to be substantially orthogonal from the first and the second openings 221, 225. The third opening 222 may be located along the portion of the breastshield and connector assembly that is distal to the breast when the breastshield 220 is positioned on a user's breast. The breastshield and connector assembly may attach to a second collection container via a fourth opening at 228. In one example embodiment, the connector 230 comprises the fourth opening 228. The fourth opening 228 may comprise a screw thread or other attachment mechanism that mates with a corresponding screw thread or other attachment mechanism on the exterior surface of the second collection container. In some example embodiments, the second collection container is a bottle for breastmilk. In other example embodiments, the second collection container is a bag for breastmilk.

The first collection container 210 comprises a first end 212 that includes a port and a second end 214 which serves as the base of the first collection container 210.

FIG. 2A depicts the first collection container 210 positioned under the third opening 222 so that the port of the first collection container 210 is in fluid communication with the third opening 222. The first collection container 210 is positioned in this manner so as to be within a first flow path 216 of expressed breast milk when the breastshield 220 is placed on a user's breast for use. Thus, a shortened or minimal flow path is formed as the first flow path 216 wherein expressed breast milk flows through a portion of the breastshield 220, through the third opening 222 of the breastshield 220, and into the first collection container 210. This first flow path 216 may also be described as a simplified flow path as the expressed breast milk does not travel through the connector 230, valve, or other various components prior to being received into a collection container. Such a simplified flow path is desirable for maximizing collection of valuable colostrum that, as previously described, is limited in quantity and has qualities rendering it more likely to become trapped in the various components as the colostrum travels along a flow path.

In the example embodiment depicted in FIG. 2A, the first collection container 210 is integral with the breastshield 220. In such an example embodiment, the first collection container 210 may be manufactured as a depressed portion of the breastshield 220. Alternatively, the first collection container 210 may be a separate piece that is attached to or inserted into the breastshield 220 or connector 230. In another embodiment, the first collection container 210 may be located inside of the breastshield 220 or connector 230.

In operation, when a breast is positioned within the interior of the breastshield 220 and breast milk is expressed, the breast milk will first flow via the simplified flow path into the first collection container 210. If expressed breast milk fills the first collection container 210 (to the first end 212) and the first collection container 210 is not emptied, any subsequently expressed breast milk will simply follow a second flow path 218 across the port at the first end 212, through the connector 230, and into the second collection container (which may be a larger collection vessel or container) attached to the connector 230 at the fourth opening 228.

Collection containers such as the first collection container 210 may comprise a variety of sizes to accommodate differing ranges of liquid (e.g., colostrum) collection. For example, the first collection container 210 may be sized to hold a volume as small as 1 milliliter (mL). Various sizes of first collection containers 210 may be envisioned to hold or accommodate volumes within the range of about 1-25 mL. A user may have a variety of sizes of first collection containers 210 available from which to select to accommodate the user's collection needs.

In some embodiments, the first collection container 210 may be made to comprise a variable volume by incorporating a mechanical element that changes the size or shape of the collection container. Such a mechanical element may comprise a corrugated wall that is expanded by a mechanical arm or spring-loaded member, a double-walled container that slides apart to expand the volume via a mechanical arm or spring-loaded member, or a flexible wall container that is stretched to a larger size by a mechanical arm or a spring-loaded member, for example.

Thus, in the embodiment shown in FIG. 2A, a small volume of breast milk may be collected without the breast milk having to pass through components such as a valve, which would risk trapping some of the breast milk or colostrum. Such a collection container 210 may serve to change the volume of the collection container to respond to different volumes of milk produced. The collection container 210 may serve to change the overall control volume within the breastpump system to keep vacuum levels stable.

Figure 2B:
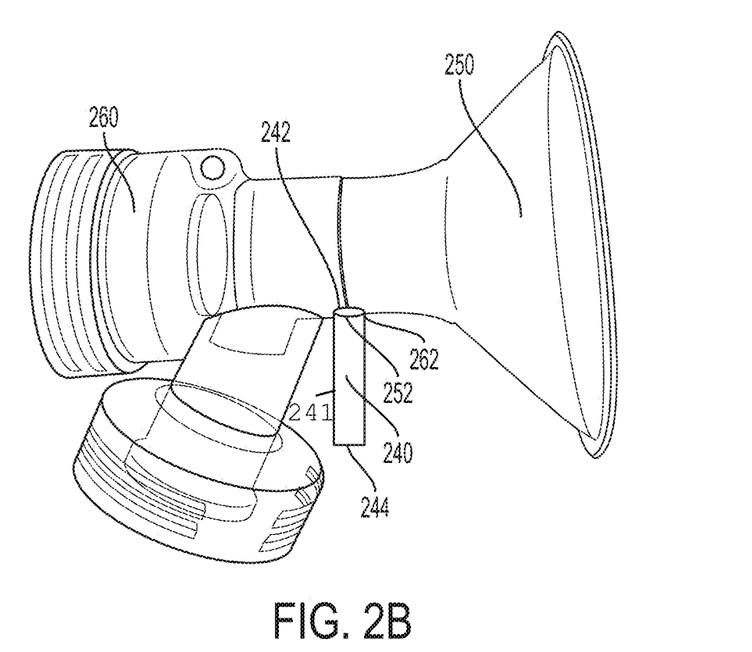
FIG. 2B is a side view of a small volume collection container attached to a breastshield and connector assembly, in accordance with an example embodiment.

FIG. 2B is a side view of a small volume collection container 240 attached to a breastshield 250, in accordance with an example embodiment. A connector 260 is also shown attached to the breastshield 250. The connector 260 may be attached to a pump (such as a vacuum pump) via tubing (not shown). The pump and tubing may be the same as or similar to the pump 130 and tubing 140 of FIG. 1.

The collection container 240 is shown to be located along the portion of the breastshield 250 that is distal to the breast when the breastshield 250 is positioned on a user's breast, at a location 262. In another example embodiment, the collection container 240 may be present at another location within the control volume, and may even be present within the breastshield. The collection container 240 comprises one or more sidewalls 241, a first end 242 comprising an opening, and a second end 244 comprising a bottom surface which serves as the base of the collection container 240.

The breastshield 250 may take the same form as or be similar in form to the breastshield 220 of FIG. 2A and may include an opening 252 that may take the same form as or be similar in form to the third opening 222. The first end 242 of the collection container 240 may be removably attachable to the opening 252 of the breastshield 250 of the breastshield and connector assembly, thereby positioning the opening 252 at the first end 242 in fluid communication with the interior of the breastshield 250. The first end 242 of the collection container 240 may comprise a screw thread and may be attached to the breastshield 250 via a corresponding screw thread on the opening 252. Other attachment means or mechanisms may also be envisioned. For example, the second end 244 may have a solid bottom, or may have a closable opening such as via a screw thread and cap, or other attachment means.

The collection container 240 may be disconnected from the breastshield 250 during or after the pumping session. To accommodate the collection container 240 being able to be disconnected during a pumping session, the opening 252 may include a cap to close the opening.

In some embodiments, the collection container 240 may be one of a set of removable collectors that the user can install based on expected volume changes. The removable containers may comprise varying volumes. In one example embodiment, the removable collection container 240 may be a syringe-style collector which may be used for later direct feeding to an infant. The collection container 240 may be sized to hold a collection volume of liquid within the range of about 1-25 milliliters.

In the examples described in FIGS. 2A-2B, the breastpump system may be configured to provide for predictable and acceptable levels of pressure (i.e., vacuum) variation. For example, vacuum variation may be limited to an acceptable range through minimizing the collection volume to a pre-determined value. Additionally, vacuum level changes inherent to the embodiments of FIGS. 2A-2B may be leveraged for increased vacuum performance as the collection containers 210, 240 fill. For example, collecting liquid inside of the control volume will increase the vacuum levels. A user may become amenable to higher vacuum performance as the user becomes used to the pump's action. Furthermore, this inherent vacuum increase may empty the breast more quickly during the later part of the pumping session, which may be desired.

Figure 3:
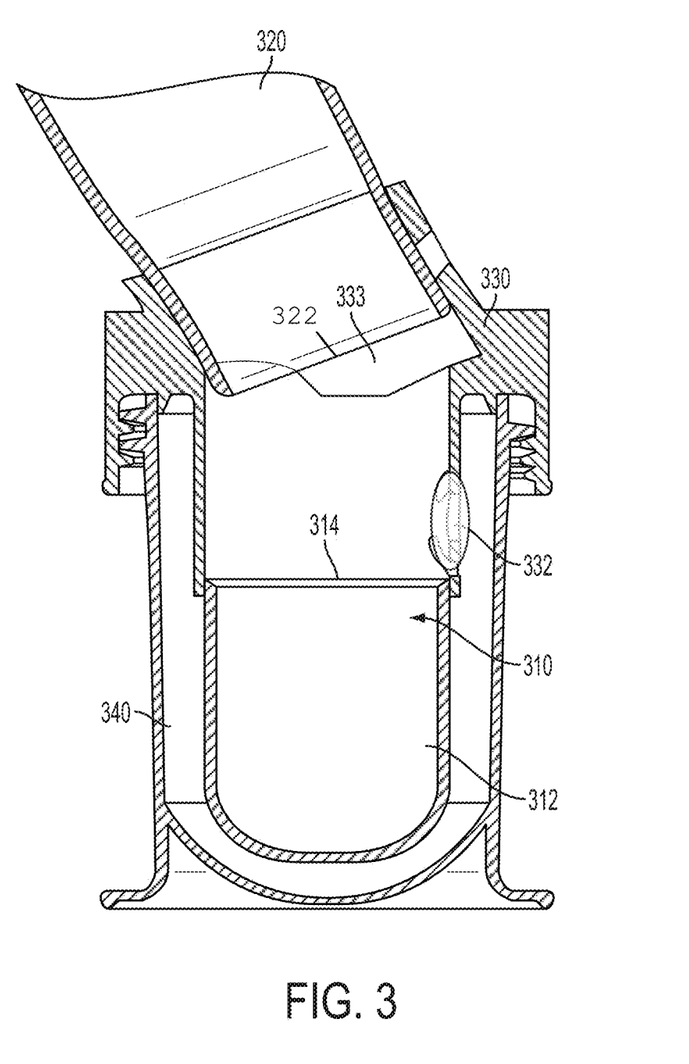
FIG. 3 is a cross-sectional view of a small volume collection container, in accordance with an example embodiment.

FIG. 3 is a cross-sectional view of a small volume collection container 310 in fluid communication with a breastshield 320 and a connector 330, in accordance with an example embodiment. FIG. 3, similarly as FIGS. 2A-2B, shows an example embodiment in which the collection container 310 is configured to collect breast milk inside of the control volume of the breastpump system and provides a simplified flow path to maximize a collection. In this embodiment, the collection container 310 is attached to a distal end 322 of the breastshield as well as to the connector 320.

In FIG. 3, the collection container 310 has a cup or bowl-like shape 312 for collecting colostrum or small volumes of breast milk or liquid. Liquid falls from an opening 333 in the connector 330 into the bowl-like shape 312 until the collection container 310 is filled to a top edge 314 of the collection container 310. An outlet valve 332 is located above or upstream of the top edge 314. The outlet valve may comprise a flap or a membrane covering an opening, in some example embodiments. This outlet valve allows air to flow out of the control volume during part of the pump's normal operation process. Thus, fluid entering the collection container 310 will not immediately pass through the outlet valve 332.

After the collection container 310 is filled to a desired level at or below the top edge 314, the collection container 310 may be removed by the user for use and/or storage. A second collection container 340 for collecting a subsequent, and in some cases, larger volume of liquid, may be attached to the connector 330 for use. The second collection container 340 may be attached so as to surround the portion of the connector 330 comprising the outlet valve 332 and to catch overflow from the collection container 310 or volumes larger than the collection container 310 can handle. These larger volumes may flow through the outlet valve 332 to reach the second collection container 340.

Because a pump's vacuum performance is dependent on the size of the control volume, collection inside of that volume may cause variations in vacuum performance. To mitigate these potential variations, a user-controlled adjustment feature may further be included to vary the control volume or an inlet valve until a predetermined, specific pressure is reached, which then causes the inlet valve to open to the atmosphere. Such a specific pressure may also be known as the activation pressure or crack pressure. The action of an inlet valve may modify or stabilize the pump's vacuum performance, and may comprise a user-controlled adjustment feature as described with reference to FIGS. 4 and 5. In such embodiments, a sensor may also be present to detect the pump's vacuum setting, an initial pressure level, and/or an incoming liquid volume. Example sensors for this type of application may include piezoelectric materials, fluid temperature sensors, and barometric sensors.

In another example embodiment, a sensor may be coupled with a mechanical or electromechanical component on the breastpump system to adjust the inlet valve activation or crack pressure or the control volume, thus stabilizing the vacuum performance automatically. Examples of such mechanical or electromechanical components may include metallic spring materials, elastomers, or shape metal such as nitinol.

Such small collection containers may be smaller in size and volume than are typically provided for use with breastpumping kits. This can provide more realistic volume expectations for the user and encourage the user that the volume produced is sufficient, such as in the example when a mother is pumping colostrum.

Moreover, fluid collection is simplified with the embodiments of FIGS. 2A-3. Milk flows directly from the breastshield into a collection container, without passing through components such as a valve and/or a membrane.

II. Example Breastpump Systems for Small Volume Collection

Figure 4:
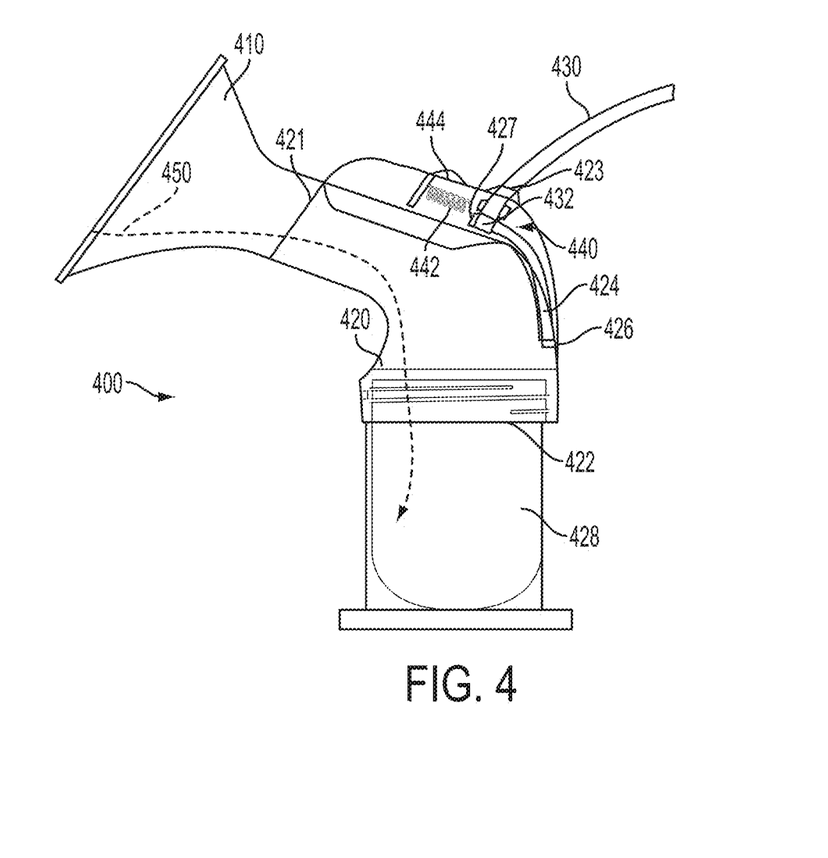
FIG. 4 is a cross-sectional view of a breastpump system, in accordance with an example embodiment.

FIG. 4 is a cross-sectional view of a breastpump system 400, in accordance with an example embodiment. The breastpump system 400 may be a breastpump kit that includes a breastshield 410, a connector 420 comprising a first end 421 and a second end 422, and a tube 430 connected to a pump mechanism (not shown). Components of the breastpump system 400 may take the same form as or be similar in form to the system 100 of FIG. 1. A collection container 428 may be provided for milk collection and can be attached at the second end 422 of the connector 420.

In the example embodiment shown in FIG. 4, a relief valve mechanism situated outside of the fluid flow path 440 is present on the connector. The relief valve mechanism 440 comprises an inlet valve (such as the inlet valve shown in FIG. 5) that opens the breastpump system 400 to the atmosphere and a spring-loaded member 442 that is configured to move when a specific pressure is reached (e.g., the crack pressure). The valve mechanism 440 may be at a location different from that shown in FIG. 4 that is not within the milk flow path. The valve mechanism 440 functions similar to a vacuum regulator. The tube 430 is attached at a first end 432 to an opening 423 in the connector 420 and is in fluid communication with the connector 420, the breastshield 410, and any attached collection container via a pathway 424. The pathway 424 may comprise a tube that is open at a first end 426 to the connector interior and a second end 427 that is attached to the spring-loaded member 442. The spring-loaded member 442 is in turn connected to an adjusting mechanism 444.

The spring-loaded member 442 may be attached to a control mechanism 444 that allows for the crack pressure of the valve to be adjusted. For example, a user can manipulate the control mechanism 444 to match a pressure for the valve 440 to the pump's vacuum setting. The control mechanism 444 may be a switch, a knob, or the like, and may comprise values indicative to a user of vacuum levels. Other desired pressure values may also be set. Safety features may be included that limit the vacuum to low levels, or to level zero, at the beginning of the pumping session to protect a user from high vacuum levels with the control mechanism 444. The control mechanism 444 may include a sensor to measure time, pressure, volume of pumped milk or another parameter important to the milk expression process. Such a sensor may be connected to an indicator that informs and/or prompts a user to adjust the vacuum level.

In operation, as breast milk is expressed into the breastshield 410 and through the connector 420 into a collection container, as shown by a simplified path 450, the vacuum level variation that occurs as the volume of the collection container is filled may be mitigated by the adjustable valve. When the vacuum level reaches the specific pressure set for the spring-loaded member 442, the spring-loaded member will operate as described in further detail below with respect to FIG. 5 to open the inlet valve.

Additionally, a sensor may be present to detect the pump's vacuum setting, an initial pressure level, and/or an incoming liquid volume. Example sensors for this type of application may include piezoelectric materials, fluid temperature sensors, and barometric sensors. Other types of sensors may also be used.

In another example embodiment, a sensor may be coupled with a mechanical or electromechanical component on the breastpump system to adjust a predetermined pressure, such as the valve activation or crack pressure, or the control volume, thus stabilizing the vacuum level automatically. Examples of such mechanical or electromechanical components may include metallic spring materials, elastomers, or shape metal such as nitinol. Other types of materials may also be used.

One benefit of the embodiment described in FIG. 4 is the valve mechanism is not placed into contact with milk flow, while remaining compatible with key features of the breastpump system, such as the breastshield and connector assembly, primary collection container and secondary collection container. Thus, fluids such as colostrum, which as previously discussed may adhere more readily to components such as inline valves, would not come into contact with the valve mechanism in FIG. 4, and the colostrum that could potentially be lost in the breastpump system would be decreased.

Additionally, fluid collection is simplified with the embodiment of FIG. 4. Milk flows directly from the breastshield into a collection container, without passing through components such as an inline valve and/or a membrane. A mother who may be inexperienced with breastpump use will not have to connect and disconnect as many parts of the breastpump kit. Furthermore, a user typically cleans pump parts after each pumping session. Since the valve and any large collection container are not in-line with the small collection volume, cleaning these components after each use may be simplified or rendered unnecessary for small-volume collection.

Yet another advantage to the embodiment of FIG. 4 is that the control mechanism of the adjustable valve is present on the connector and/or the breastshield of the breastpump system. A user can thus make adjustments to the pressure on these components instead of having to interface directly with the main pump unit during pumping. Additionally, pressure adjustments can be made independently for each breast.

Figure 5:
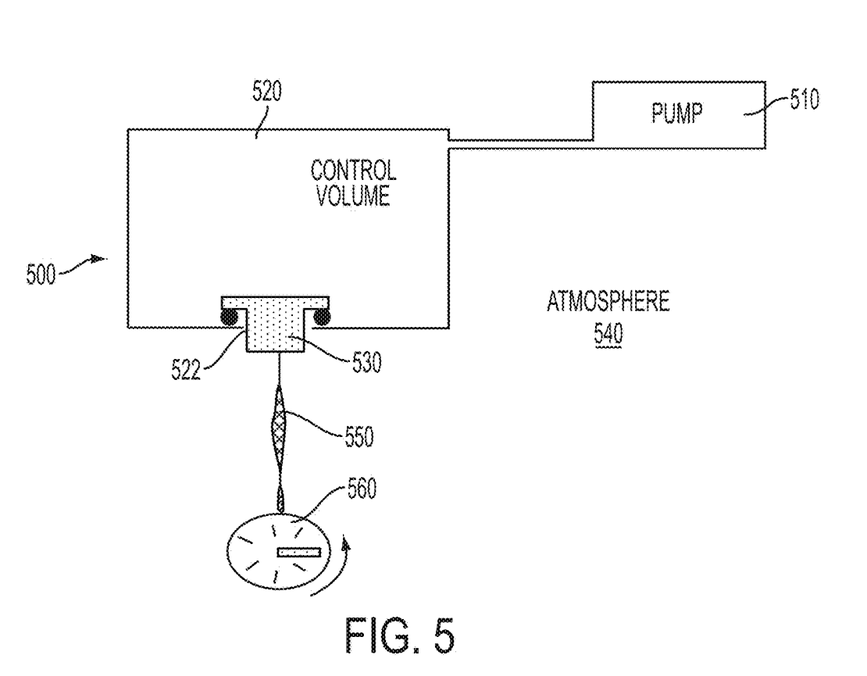
FIG. 5 is a schematic of an adjustable valve that may be used with the breastpump system of FIG. 4, in accordance with an example embodiment.

FIG. 5 is a schematic 500 of an adjustable valve configuration that may be used with the breastpump kit of FIG. 4, in accordance with an example embodiment. In FIG. 5, a pump 510 is in fluid communication with a control volume 520, such as that within the assembly of FIG. 4. A tube such as the tube 430 may provide the fluid connection between the pump 510 and the control volume 520.

In the schematic 500, a sealing element 530 covers an opening 522 that connects the control volume 520 to the atmosphere 540, and is attached to an elastic element 550, which in turn is attached to an adjustment mechanism 560. The elastic element 550 may be the same or similar to the spring-loaded member 442 of FIG. 4. The adjustment mechanism 560 may be the same or similar to the control mechanism 444 of FIG. 4.

The sealing element 530 may be an o-ring, in one example embodiment. Other types of sealing elements may also be envisioned, however.

In operation, a user adjusts the adjustment mechanism 560 to a desired vacuum level for operation of the breastpump system. Manual manipulation of the adjustment mechanism 560 changes the force on the elastic element 550. The adjustment mechanism 560 may be a switch, a knob, or the like, and may comprise values indicative to a user of vacuum levels. When the spring force of the elastic element 550 holding the sealing element 530 in place is exceeded by the vacuum-generated force from the pump 510, the sealing element 530 moves to uncover the opening between the control volume 520 and the atmosphere 540. Other adjustable valve mechanisms that combine elastic elements, rigid elements and inlet orifices may also be envisioned.

Figure 6:
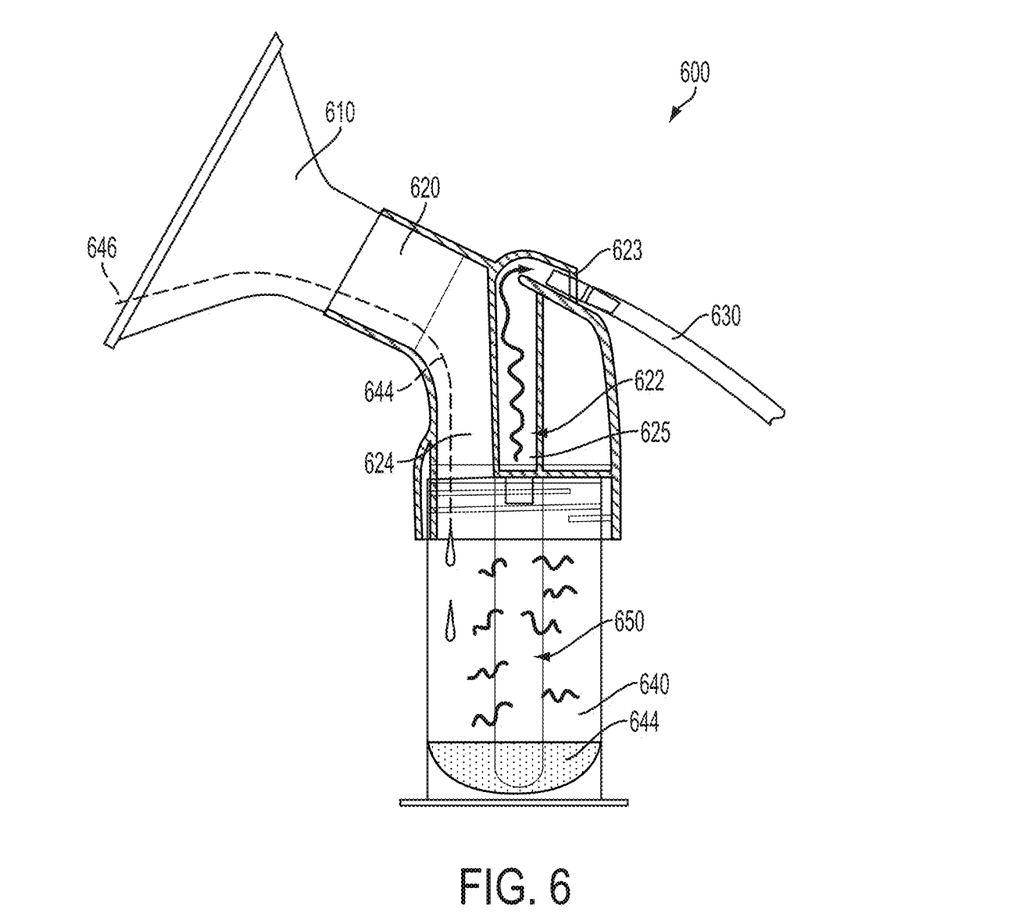
FIG. 6 is a cross-sectional view of a breastpump system, in accordance with an example embodiment.

FIG. 6 is a cross-sectional view of a breastpump system 600, in accordance with an example embodiment. The breastpump system 600 comprises a breastshield 610, a connector 620 attached to the breastshield 610, a pump tube 630 attached to the connector 620, and a collection container 640 that is also attached to the connector 620.

The connector 620 includes an air-path 622 that has as an opening 623 between an interior 624 of the connector 620 and the atmosphere, and extends via a tube 625 through the interior 624 of the connector 620. The pump tube 630 may be inserted into the opening 623. A perforated member, such as a gas-permeable membrane 650 may be attached to the tube 625 and may extend into the attached collection container 640.

The embodiment of FIG. 6 provides for mechanically sensing of the incoming liquid volume and using the presence of the incoming liquid to progressively adjust the vacuum level. Breast pumps evacuate a control volume through an inlet orifice, usually the tubing inner diameter. If the orifice is too small, the pump's ability to draw air will be stunted, and less vacuum will be generated.

The perforated member (represented here as a gas-permeable membrane) 650 comprises a series of vacuum inlet holes that allow for air passage therethrough but are too small for the passage or penetration of liquids such as breast milk (including colostrum). The perforated member 650 serves as an extension of the tubing inner diameter. Any submerged portion of the perforated member 600 will not be available for air flow, thus decreasing the amount of air flow as the liquid level increases. The increasing liquid also decreases the control volume, which potentially increases vacuum if left unmitigated. The decreasing inlet vacuum orifice and decreasing control volume may counterbalance each other and keep the vacuum level stable.

Liquid 644 flows along an example flow path 646 into the collection container 640. As the liquid 644 flows and fills the collection container 640, the permeable membrane 650 is gradually covered, controlling vacuum variability as described above.

Other embodiments for mechanically sensing incoming liquid and controlling vacuum levels may be envisioned. For example, a floating member that rises with the liquid level may be connected to another member that enlarges the control volume, reduces the vacuum inlet orifice, or increases the vacuum relief orifice as the liquid fills a collection container. In another example, the mass of the incoming liquid may be used as a signal to modify control volume or functional orifices.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A system for small volume milk collection comprising: a breastshield having a first opening arranged at a first end for receiving at least a portion of a breast, a second opening at a second end configured to mate with a connector, a third opening arranged at a junction between the first opening and the second opening and extending through a side of the breastshield and a fourth opening arranged between the third opening and the second end, wherein the third opening is positioned within a first flow path for expressed breast milk and the fourth opening is positioned within a second flow path for the expressed breast milk, wherein the second flow path extends across the third opening to the fourth opening such that the first flow path is shorter than the second flow path; and a first collection container having a first end configured for removable attachment to the third opening of the breastshield, the fourth opening configured to connect to a second collection container; the first collection container being in fluid communication with an interior of the breastshield when attached to the third opening to form a liquid flow path for the expressed breast milk thereby, wherein the first collection container is configured to hold a volume of expressed breast milk not exceeding about 25 milliliters.

2. The system of claim 1, further comprising a set of collection containers of different sizes, each collection container of the set being configured to serve as the first collection container.

3. The system of claim 1, wherein the first collection container comprises a mechanical element that changes the volume of the first collection container by changing the size or shape of the first collection container.

4. The system of claim 1, wherein the first collection container comprises a variable volume element that changes the size or shape of the first collection container.

5. The system of claim 1, wherein the first collection container is a syringe-style collector.

6. A method comprising: receiving colostrum and expressed breast milk via a breastshield of a breastpump system during a pumping operation, wherein the breastshield has a first opening arranged at a first end for receiving at least a portion of a breast, a second opening at a second end configured to mate with a connector, a third opening arranged at a junction between the first opening and the second opening and extending through a side of the breastshield and a fourth opening arranged between the third opening and the second end, wherein the third opening is positioned within a first flow path for expressed breast milk and the fourth opening is positioned within a second flow path for the expressed breast milk, wherein the second flow path extends across the third opening to the fourth opening such that the first flow path is shorter than the second flow path; collecting colostrum in a first collection container via the first flow path through an interior of the breastshield into the third opening, wherein the first collection container is a syringe-style container coupled to the third opening, wherein the syringe-style container is configured to be reachable by a user's hand while the user's hand holds the breastshield; and collecting the expressed breast milk in a second collection container via the second flow path through the breastshield into the fourth opening.

7. The method of claim 6, further comprising:
providing a suction force to the breastshield;
removing the syringe-style container from the breastshield during or after the pumping session.

* * * * *